United States Patent [19]

Takemoto et al.

[11] Patent Number: 5,424,476

[45] Date of Patent: Jun. 13, 1995

[54] METHOD FOR PREPARING AMINO ACID ESTERS

[75] Inventors: Tadashi Takemoto; Hideo Takeda, both of Kawasaki, Japan

[73] Assignee: Central Research Laboratories Ajinomoto Co., Inc., Kawasaki, Japan

[21] Appl. No.: 194,635

[22] Filed: Feb. 10, 1994

Related U.S. Application Data

[63] Continuation of Ser. No. 982,123, Nov. 25, 1992, abandoned.

[30] Foreign Application Priority Data

Nov. 28, 1991 [JP] Japan ................................ 3-314585

[51] Int. Cl.$^6$ ............................................. C07C 229/08
[52] U.S. Cl. ......................................... 560/38; 560/171
[58] Field of Search ................................. 560/38, 171

[56] References Cited

U.S. PATENT DOCUMENTS 4,680,403  7/1987  Hisamitsu et al. .................. 546/247

OTHER PUBLICATIONS

CRC Hand book of Chemistry and Physic 59th edition 1978–1979 pp. D40(55), D44(113).
Organic Chemistry; T. W. Graham Solomons John Wiley & Sons, 1980.
"Organic Chemistry"; Andrew Streitwiser, Jr. Clayton H. Heathcock pp. 441–444 and 827–828 1976.

*Primary Examiner*—José G. Dees
*Assistant Examiner*—Samuel Barts
*Attorney, Agent, or Firm*—Oblon, Spivak, McClelland, Maier & Neustadt

[57] ABSTRACT

A method for preparing an amino acid ester with sulfuric acid as the catalyst in high yield, in which a mixture of amino acid, sulfuric acid and an alcohol is heated while adding the alcohol as a liquid or gas to the reaction mixture and alcohol from the reaction mixture is distilled off.

6 Claims, No Drawings

METHOD FOR PREPARING AMINO ACID ESTERS

This is a continuation of application Ser. No. 07/982,123, filed Nov. 25, 1992, now abandoned.

BACKGROUND OF THE INVENTION

1. Field of the Invention

The present invention relates to a method for preparing amino acid esters using sulfuric acid as the catalyst.

2. Discussion of the Background

L-phenylalanine methyl ester is an important intermediate for preparing α-L-aspartyl-L-phenylalanine methyl ester which has been in the spotlight lately as a low-calorie sweetener. A method of esterifying amino acids with sulfuric acid as the catalyst is known which involves heating an amino acid in an alcohol in the presence of sulfuric acid. This process is described in U.S. Pat. No. 4,680,403. However, it has a serious drawback in that the yield is low. The purpose of the present invention is to provide a method for preparing amino acids in higher yield.

DETAILED DESCRIPTION OF THE PREFERRED EMBODIMENTS

The present inventors have discovered that the esterification yield is significantly improved when an amino acid is heated in an alcohol in the presence of sulfuric acid while adding the alcohol as a liquid or gas to the reaction mixture and distilling off alcohol from the reaction mixture. On the basis of this finding, they have completed the present invention.

The amino acid to be used as a raw material for the method may be any optical isomer, i.e. the dextrorotary (D), levorotary (L) or racemic (DL) form. Examples of the alcohol are lower alcohols such as methanol, ethanol, propanol, isopropanol, butanol, pentanol and hexanol. Especially preferred are methanol and ethanol.

In accordance with the present invention, an amino acid is first dispersed in an amount of alcohol from 1 to 10 molar equivalents relative to the quantity of the amino acid. Then 0.5 molar equivalents or more of sulfuric acid, relative to the amino acid is added thereto. Afterwards, the same alcohol is added to and distilled off from the reaction mixture with heating. The amount of sulfuric acid to be used may be a large excess relative to the amino acid or may be 0.5 molar equivalents or more. In general, it is advantageously from 0.5 to 2.0 molar equivalents thereto for industrial practice. The amount of alcohol to be added may be a large excess relative to the amino acid or may be 10 molar equivalents or more. Preferably, it is from 20 to 60 molar equivalents thereto.

The alcohol may be added to the reaction mixture as a liquid or may be added as a vapor generated in a separate device. The alcohol may be added either continuously or intermittently little by little. The addition speed is not specifically defined. Preferably, the total of the addition time is within the range of from 2 hours to 6 hours. The reaction temperature is 60° C. or higher, preferably from 80° C. to 100° C.

Other features of the invention will become apparent in the course of the following descriptions of exemplary embodiments which are given for illustration of the invention and are not intended to be limiting thereof.

EXAMPLE 1

82.6 g (0.5 mol) of L-phenylalanine was dispersed in 160 ml of methanol, and 55.0 g (0.55 mol) of 98% sulfuric acid was added thereto. The resulting mixture was kept at 85° C. and 730 ml of methanol was continuously added thereto over a period of 4 hours while almost the same amount of methanol was distilled off from the reaction mixture. The reaction solution was subjected to high performance liquid chromatography (hereinafter referred to as HPLC) to determine the amount of L-phenylalanine methyl ester formed. The yield was 98.6% based on L-phenylalanine.

Comparative Example 1

82.6 g (0.5 mol) of L-phenylalanine was dispersed in 160 ml of methanol, and 55.0 g (0.55 mol) of 98% sulfuric acid was added thereto. The mixture was heated under reflux at 85° C. for 4 hours. The reaction solution was subjected to HPLC to determine the amount of L-phenylalanine methyl ester formed. The yield was 83.2% based on L-phenylalanine.

EXAMPLE 2

82.6 g (0.5 mol) of L-phenylalanine was dispersed in 100 ml of methanol, and 65.0 g (0.65 mol) of 98% sulfuric acid was added thereto. The resulting mixture was kept at 89° C. and 790 ml of methanol was continuously added thereto over a period of 4 hours while almost the same amount of methanol was distilled off from the reaction system. The reaction solution was subjected to HPLC to determine the yield of L-phenylalanine methyl ester formed which was 99.0% based on L-phenylalanine.

EXAMPLE 3

66.7 g (0.5 mol) of L-aspartic acid was dispersed in 160 ml of methanol, and 55.0 g (0.55 mol) of 98% sulfuric acid was added thereto. The resulting mixture was kept at 89° C. and 730 ml of methanol was continuously added thereto over a period of 4 hours while almost the same amount of methanol was distilled off from the reaction mixture. The reaction solution was subjected to HPLC to determine the yield of dimethyl L-aspartate formed which was 98.5% based on L-aspartic acid.

EXAMPLE 4

82.6 g (0.5 mol) of L-phenylalanine was dispersed in 100 ml of ethanol, and 65.0 g (0.65 mol) of 98% sulfuric acid was added thereto. The resulting mixture was kept at 90° C. and 790 ml of ethanol was continuously added thereto over a period of 3.5 hours while almost the same amount of ethanol was distilled off from the reaction mixture. The reaction solution was subjected to HPLC to determine the yield of L-phenylalanine ethyl ester formed, which was 99.9% based on L-phenylalanine.

Comparative Example 2

82.6 g (0.5 mol) of L-phenylalanine was dispersed in 160 ml of ethanol, and 65.0 g (0.65 mol) of 98% sulfuric acid was added thereto. The mixture was heated under reflux at 90° C. for 3.5 hours. The reaction solution was subjected to HPLC to determine the yield of L-phenylalanine ethyl ester formed which was 78.1% based on L-phenylalanine.

EXAMPLE 5

82.6 g (0.5 mol) of L-phenylalanine was dispersed in 160 ml of methanol, and 55.0 g (0.55 mol) of 98% sulfuric acid was added thereto. The resulting mixture was kept at 85° C. and methanol vapor generated by heating 730 ml of methanol was continuously added thereto over a period of 4 hours while almost the same amount of methanol was distilled off from the reaction mixture. The reaction solution was subjected to HPLC to determine the yield of L-phenylalanine methyl ester formed which was 98.5% based on L-phenylalanine.

EXAMPLE 6

82.6 g (0.5 mol) of L-phenylalanine was dispersed in 100 ml of methanol, and 55.0 g (0.55 mol) of 98% sulfuric acid was added thereto. The resulting mixture was kept at 88° C. and methanol vapor generated by heating 850 ml of methanol was continuously added thereto over a period of 4 hours while almost the same amount of methanol was distilled off from the reaction system. The reaction solution was subjected to HPLC to determine the yield of L-phenylalanine methyl ester formed. The yield was 98.8% based on L-phenylalanine.

EXAMPLE 7

58.6 g (0.5 mol) of L-valine was dispersed in 160 ml of methanol, and 55.0 g (0.55 mol) of 98% sulfuric acid was added thereto. The resulting mixture was kept at 85° C. and methanol was added portionwise in 24 portions of 30 ml each at regular intervals of 10 minutes, while almost the same amount of methanol was distilled off from the reaction mixture. The reaction solution was subjected to HPLC to determine the yield of L-valine methyl ester formed which was 96.7% based on L-valine.

EXAMPLE 8

44.5 g (0.5 mol) of L-alanine was dispersed in 160 ml of methanol, and 55.0 g (0.55 mol) of 98% sulfuric acid was added thereto. The mixture was kept at 85° C., and 730 ml of methanol was continuously added thereto over a period of 4 hours while almost the same amount of methanol was distilled off from the reaction mixture. The reaction solution was subjected to HPLC to determine the yield of L-alanine methyl ester formed. The yield was 98.1% based on L-alanine.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. In a method for preparing an amino acid ester by heating a mixture consisting of an amino acid, methanol and sulfuric acid, the improvement comprising:
    removing methanol from the reaction mixture while adding methanol as a liquid or gas in approximately equal amounts.
2. The method as claimed in claim 1, in which the methanol is continuously added to and distilled off from the reaction mixture.
3. The method as claimed in claim 1, in which the amino acid is L-phenylalanine.
4. The method as claimed in claim 1, in which the amino acid is L-aspartic acid.
5. The method as claimed in claim 1, in which the methanol is added portionwise.
6. The process of claim 1 wherein the reaction temperature is up to 89° C.

* * * * *